(12) United States Patent
Clausen et al.

(10) Patent No.: US 9,168,158 B2
(45) Date of Patent: *Oct. 27, 2015

(54) SMOOTH ROLLOVER INSOLE FOR PROSTHETIC FOOT

(71) Applicant: Ossur hf, Reykjavik (IS)

(72) Inventors: Arinbjorn Viggo Clausen, Reykjavik (IS); Grimur Jonsson, Vogar (IS); Christophe Lecomte, Reykjavik (IS)

(73) Assignee: Össur hf, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 14/201,361

(22) Filed: Mar. 7, 2014

(65) Prior Publication Data

US 2014/0257523 A1    Sep. 11, 2014

Related U.S. Application Data

(63) Continuation of application No. 12/410,147, filed on Mar. 24, 2009, now Pat. No. 8,685,109.

(60) Provisional application No. 61/077,380, filed on Jul. 1, 2008.

(51) Int. Cl.
*A61F 2/66* (2006.01)
*A61F 2/76* (2006.01)
(Continued)

(52) U.S. Cl.
CPC ... *A61F 2/66* (2013.01); *A61F 2/76* (2013.01); *A61F 2002/30014* (2013.01); *A61F 2002/30324* (2013.01); *A61F 2002/30359* (2013.01); *A61F 2002/30433* (2013.01); *A61F 2002/5001* (2013.01); *A61F 2002/5003* (2013.01);

(Continued)

(58) Field of Classification Search
CPC ..... A61F 2/60; A61F 2/66; A61F 2002/6614; A61F 2002/6642; A61F 2002/665; A61F 2002/6657; A61F 2002/6678
USPC ...................................................... 623/47–56
See application file for complete search history.

(56) References Cited

U.S. PATENT DOCUMENTS

| 549,405 A | 11/1895 | Marks |
| 1,649,773 A | 11/1927 | Witmyer |

(Continued)

FOREIGN PATENT DOCUMENTS

| EP | 1 149 568 | 10/2001 |
| GB | 120462 | 11/1918 |

(Continued)

OTHER PUBLICATIONS

Apr. 20, 2010 Final Office Action for U.S. Appl. No. 11/139,009, filed May 26, 2005.

(Continued)

*Primary Examiner* — Marcia Watkins
(74) *Attorney, Agent, or Firm* — Knobbe, Martens, Olson & Bear, LLP.

(57) ABSTRACT

A prosthetic foot includes a foot member, a heel member operatively coupled to the foot member. At least one of the heel member and foot member define an arch portion that faces a support surface that the prosthetic foot contacts during use. An insole member contacts said arch portion, the insole member configured to facilitate a rollover of the prosthetic foot in at least one of a lateral-medial and a medial-lateral direction during ambulation.

19 Claims, 17 Drawing Sheets

(51) Int. Cl.
*A61F 2/30* (2006.01)
*A61F 2/50* (2006.01)

(52) U.S. Cl.
CPC ... *A61F2002/5007* (2013.01); *A61F 2002/665* (2013.01); *A61F 2002/6614* (2013.01); *A61F 2002/6621* (2013.01); *A61F 2002/6642* (2013.01); *A61F 2002/6657* (2013.01); *A61F 2002/6671* (2013.01); *A61F 2002/6678* (2013.01); *A61F 2002/6685* (2013.01); *A61F 2002/7695* (2013.01); *A61F 2220/0033* (2013.01); *A61F 2220/0041* (2013.01); *A61F 2250/0018* (2013.01); *A61F 2250/0036* (2013.01)

(56) References Cited

U.S. PATENT DOCUMENTS

| | | | |
|---|---|---|---|
| 2,197,093 A | 4/1940 | Campbell | |
| 2,556,525 A | 5/1951 | Drennon | |
| 2,692,392 A | 10/1954 | Bennington et al. | |
| 3,551,914 A | 1/1971 | Woodall | |
| 3,784,988 A | 1/1974 | Trumpler | |
| 3,874,004 A | 4/1975 | May | |
| 4,328,594 A * | 5/1982 | Campbell et al. | 623/55 |
| 4,547,913 A | 10/1985 | Phillips | |
| 4,652,266 A | 3/1987 | Truesdell | |
| 4,756,098 A | 7/1988 | Boggia | |
| 4,865,612 A | 9/1989 | Arbogast et al. | |
| 4,892,553 A | 1/1990 | Prahl | |
| 4,892,554 A | 1/1990 | Robinson | |
| 4,911,724 A | 3/1990 | Fikes | |
| 4,959,073 A | 9/1990 | Merlette | |
| 5,019,109 A | 5/1991 | Volsin | |
| 5,062,859 A | 11/1991 | Naeder | |
| 5,112,356 A | 5/1992 | Harris et al. | |
| 5,156,632 A | 10/1992 | Wellershaus | |
| 5,181,932 A | 1/1993 | Phillips | |
| 5,201,775 A | 4/1993 | Arbogast et al. | |
| 5,219,365 A | 6/1993 | Sabolich | |
| 5,258,038 A | 11/1993 | Robinson et al. | |
| 5,290,319 A | 3/1994 | Phillips | |
| 5,376,133 A | 12/1994 | Gramnas | |
| 5,387,246 A | 2/1995 | Phillips | |
| 5,405,410 A | 4/1995 | Arbogast et al. | |
| 5,425,781 A | 6/1995 | Allard et al. | |
| 5,443,522 A | 8/1995 | Hiemisch | |
| 5,443,527 A | 8/1995 | Wilson | |
| 5,443,529 A | 8/1995 | Phillips | |
| 5,507,838 A | 4/1996 | Chen | |
| 5,545,234 A | 8/1996 | Collier, Jr. | |
| 5,549,711 A | 8/1996 | Bryant | |
| 5,593,453 A | 1/1997 | Ahlert et al. | |
| 5,701,686 A | 12/1997 | Berr et al. | |
| 5,728,171 A | 3/1998 | Bryant, Jr. et al. | |
| 5,888,239 A | 3/1999 | Wellershaus et al. | |
| 5,897,594 A | 4/1999 | Martin et al. | |
| 5,899,944 A | 5/1999 | Phillips | |
| 6,029,374 A | 2/2000 | Herr et al. | |
| 6,083,265 A | 7/2000 | Shorter et al. | |
| 6,099,572 A | 8/2000 | Mosler et al. | |
| 6,197,067 B1 | 3/2001 | Shorter et al. | |
| 6,206,934 B1 | 3/2001 | Phillips | |
| 6,241,776 B1 | 6/2001 | Christensen | |
| 6,261,324 B1 | 7/2001 | Merlette | |
| 6,280,479 B1 | 8/2001 | Phillips | |
| 6,290,730 B1 | 9/2001 | Pitkin et al. | |
| 6,387,134 B1 * | 5/2002 | Parker et al. | 623/55 |
| 6,398,818 B1 | 6/2002 | Merlette et al. | |
| 6,402,790 B1 | 6/2002 | Celebi | |
| 6,443,995 B1 | 9/2002 | Townsend et al. | |
| 6,663,673 B2 | 12/2003 | Christensen | |
| 6,669,737 B2 | 12/2003 | Mosler et al. | |
| 6,699,295 B2 | 3/2004 | Lee et al. | |
| 6,712,860 B2 | 3/2004 | Rubie et al. | |
| 6,719,807 B2 | 4/2004 | Harris | |
| 6,764,522 B1 | 7/2004 | Cehn | |
| 6,811,571 B1 | 11/2004 | Phillips | |
| 6,929,665 B2 | 8/2005 | Christensen | |
| 6,969,408 B2 | 11/2005 | Lecomte et al. | |
| 7,108,723 B2 | 9/2006 | Townsend et al. | |
| 7,181,866 B2 | 2/2007 | Braunschweiler | |
| 7,181,868 B2 | 2/2007 | Auger et al. | |
| 7,279,011 B2 | 10/2007 | Phillips | |
| 7,347,877 B2 | 3/2008 | Clausen et al. | |
| 7,419,509 B2 | 9/2008 | Christensen | |
| 7,578,852 B2 | 8/2009 | Townsend et al. | |
| 7,618,464 B2 | 11/2009 | Christensen | |
| 7,727,285 B2 | 6/2010 | Christensen et al. | |
| 7,736,394 B2 | 6/2010 | Bedard et al. | |
| 7,846,213 B2 | 12/2010 | Lecomte et al. | |
| 8,685,109 B2 * | 4/2014 | Clausen et al. | 623/55 |
| 2002/0038522 A1 | 4/2002 | Houser et al. | |
| 2002/0040249 A1 | 4/2002 | Phillips | |
| 2002/0082713 A1 | 6/2002 | Townsend et al. | |
| 2002/0087216 A1 | 7/2002 | Atkinson et al. | |
| 2002/0116072 A1 | 8/2002 | Rubie et al. | |
| 2002/0128727 A1 | 9/2002 | Merlette et al. | |
| 2002/0183860 A1 | 12/2002 | Wilkinson | |
| 2003/0045944 A1 | 3/2003 | Mosler et al. | |
| 2003/0144745 A1 * | 7/2003 | Phillips | 623/55 |
| 2004/0162623 A1 | 8/2004 | Phillips | |
| 2005/0033451 A1 | 2/2005 | Aigner et al. | |
| 2005/0038524 A1 | 2/2005 | Jonsson et al. | |
| 2005/0038525 A1 | 2/2005 | Doddroe et al. | |
| 2005/0060045 A1 | 3/2005 | Smith et al. | |
| 2005/0071018 A1 | 3/2005 | Phillips | |
| 2005/0261783 A1 | 11/2005 | Geilman et al. | |
| 2005/0267603 A1 | 12/2005 | Lecomte et al. | |
| 2006/0015192 A1 | 1/2006 | Clausen et al. | |
| 2006/0069450 A1 | 3/2006 | McCarvill et al. | |
| 2006/0167563 A1 | 7/2006 | Johnson et al. | |
| 2006/0247794 A1 | 11/2006 | Doddroe et al. | |
| 2007/0027557 A1 | 2/2007 | Jonsson et al. | |
| 2007/0106395 A9 | 5/2007 | Clausen et al. | |
| 2008/0046096 A1 | 2/2008 | Bedard et al. | |
| 2008/0188951 A1 * | 8/2008 | Christensen et al. | 623/55 |
| 2009/0012630 A1 | 1/2009 | Molser et al. | |
| 2009/0287315 A1 | 11/2009 | Lecomte et al. | |
| 2009/0306792 A1 | 12/2009 | Lecomte et al. | |

FOREIGN PATENT DOCUMENTS

| | | |
|---|---|---|
| WO | WO 02/02034 | 1/2002 |
| WO | WO 02/38087 | 5/2002 |
| WO | WO 02/051342 | 7/2002 |
| WO | WO 2004/032809 | 4/2004 |
| WO | WO 2005/079712 | 9/2005 |
| WO | WO 2005/117749 | 12/2005 |
| WO | WO 2006/034285 | 3/2006 |
| WO | WO 2007/085228 | 8/2007 |

OTHER PUBLICATIONS

Dec. 6, 2010 Office Action of U.S. Appl. No. 11/139,009, filed May 26, 2005.

Jul. 27, 2010 Notice of Allowance for U.S. Appl. No. 10/987,940, filed Nov. 12, 2004.

Jun. 29, 2010 Office Action for U.S. Appl. No. 11/139,009, filed May 26, 2005.

Nov. 27, 2009 Office Action for U.S. Appl. No. 10/987,940, filed Nov. 12, 2004.

Willow Wood™ Impulse® Foot, believed to have been available by 2004, http://www.willowwoodco.com/products-and-services/feet/moderate-activity/impulse, last visited May 5, 2011.

Nobbe Orthopedics, Inc., *Prosthetic & Orthotic Update* No. 40, © 2004, available at http://www.nobbeorthopedics.com/ns_pdf/nobbe_news_40.pdf, last visited May 5, 2011.

United States Patent and Trademark Office, Office Action for U.S. Appl. No. 10/987,940, Nov. 13, 2008.

(56) References Cited

OTHER PUBLICATIONS

United States Patent and Trademark Office, Office Action for U.S. Appl. No. 10/987,940, Apr. 8, 2008.
United States Patent and Trademark Office, Office Action for U.S. Appl. No. 10/987,940, Apr. 3, 2009.
ISA, International Search Report for PCT/US2009/048970, Sep. 15, 2009.
USPTO, Office Action for U.S. Appl. No. 11/139,009, Sep. 29, 2009.
Oct. 10, 2011 Office Action for European Patent Application No. 09 774 195 filed on Jun. 26, 2009.
May 24, 2011 Office Action for U.S. Appl. No. 11/139,009, filed May 26, 2005.
Jan. 28, 2014 Office Action for Chinese Patent Application No. 200980134201.8 filed on Jun. 26, 2009.

* cited by examiner

SMOOTH ROLLOVER INSOLE FOR PROSTHETIC FOOT

RELATED APPLICATION

This application is a continuation of U.S. application Ser. No. 12/410,147, filed on Mar. 24, 2009, and entitled "SMOOTH ROLLOVER INSOLE FOR PROSTEHTIC FOOT," which claims the benefit of priority under 35 U.S.C. §119(e) of U.S. Provisional Application No. 61/077,380, filed on Jul. 1, 2008, and entitled "SMOOTH ROLLOVER INSOLE FOR PROSTHETIC FOOT," the entirety of each of which is hereby incorporated herein by reference to be considered a part of this specification.

BACKGROUND OF THE INVENTION

1. Field of the Invention

The present invention is directed to a prosthetic foot and more particularly to a prosthetic foot with an insole that facilitates a smooth rollover of the prosthetic foot during use.

2. Description of the Related Art

Prosthetic feet of different designs are well known in the art. The various conventional designs have sought to solve various limitations associated with prosthetic feet.

Common to many conventional prosthetic foot designs is the desire to approximate the feel and fluid range of motion of a human foot's natural stride. One aspect of said natural stride is the ability to fluidly transition from heel-strike to toe-off during motion of the foot.

Some conventional designs attempt to provide said fluid transition by incorporating springs of different types (e.g., leaf spring) and shapes (e.g., C-shaped, U-shaped) to store and release energy during motion of the prosthetic foot. However, such energy-storing and energy-releasing designs do not provide the desired degree of stride fluidity and rollover characteristics during foot motion that approximate the motion of a natural human foot. For example, conventional prosthetic foot designs can experience a sudden impact when the metatarsal portion of the prosthetic foot initially contacts the ground, where the load center of the prosthetic foot travels anteriorly extremely fast, thereby providing an unnatural and uncomfortable gait during ambulation.

Accordingly, there is a need for a prosthetic foot with improved stride fluidity and rollover performance.

SUMMARY OF THE INVENTION

In accordance with one embodiment, a prosthetic foot is provided, comprising a foot member and a heel member attached to the foot member, one or both of the foot member and the heel member comprises an arch portion defining a concave surface that faces a support surface the prosthetic foot contacts during ambulation. The prosthetic foot also comprises an insole member configured to contact the arch portion, the insole member having a bottom surface that contacts the support surface during motion of the prosthetic foot, wherein the bottom surface has a concave shape when the prosthetic foot is unloaded, has a generally flat shape when the foot is loaded and in a stand-still position, and has a convex bottom surface upon heel strike of the prosthetic foot.

In accordance with another embodiment, a prosthetic foot is provided comprising a foot member and a heel member operatively coupled to the foot member, wherein one or both of the heel member and foot member defines a contoured portion that faces a support surface that the prosthetic foot contacts during ambulation. The prosthetic foot also comprises an insole member configured to contact said contoured portion, the insole member configured to facilitate a rollover of the prosthetic foot in at least one of a lateral-medial and medial-lateral direction during ambulation, wherein the insole member is configured to maintain one or both of the heel and foot members in continuous contact with the support surface from at least a heel-strike position to a mid-stance position during ambulation of the prosthetic foot.

In accordance with still another embodiment, a prosthetic foot is provided comprising a foot member defining a contoured portion that faces a support surface that the prosthetic foot contacts during use. The prosthetic foot also comprises a foot cover configured to receive the foot member therein, the foot cover comprising insole member configured to contact said contoured portion during ambulation of the prosthetic foot, the insole member configured to facilitate a rollover of the prosthetic foot in at least one of a lateral-medial and medial-lateral direction during ambulation, wherein the insole member is configured to maintain the foot member in generally continuous contact with the support surface from at least a heel-strike position to a mid-stance position during ambulation of the prosthetic foot.

In accordance with yet another embodiment, a prosthetic foot is provided. The prosthetic foot comprises a body generally shaped like a natural human foot defining a cavity therein configured to receive a prosthetic foot member defining a portion that faces a support surface that the prosthetic foot contacts during use. The prosthetic foot also comprises an insole member configured to contact said portion, the insole member configured to facilitate a rollover of the prosthetic foot in at least one of a lateral-medial and medial-lateral direction during ambulation, wherein the insole member is configured to maintain the prosthetic foot member in generally continuous contact with the support surface from at least a heel-strike position to a mid-stance position during ambulation of the prosthetic foot.

DETAILED DESCRIPTION OF THE PREFERRED EMBODIMENTS

Figure 1:
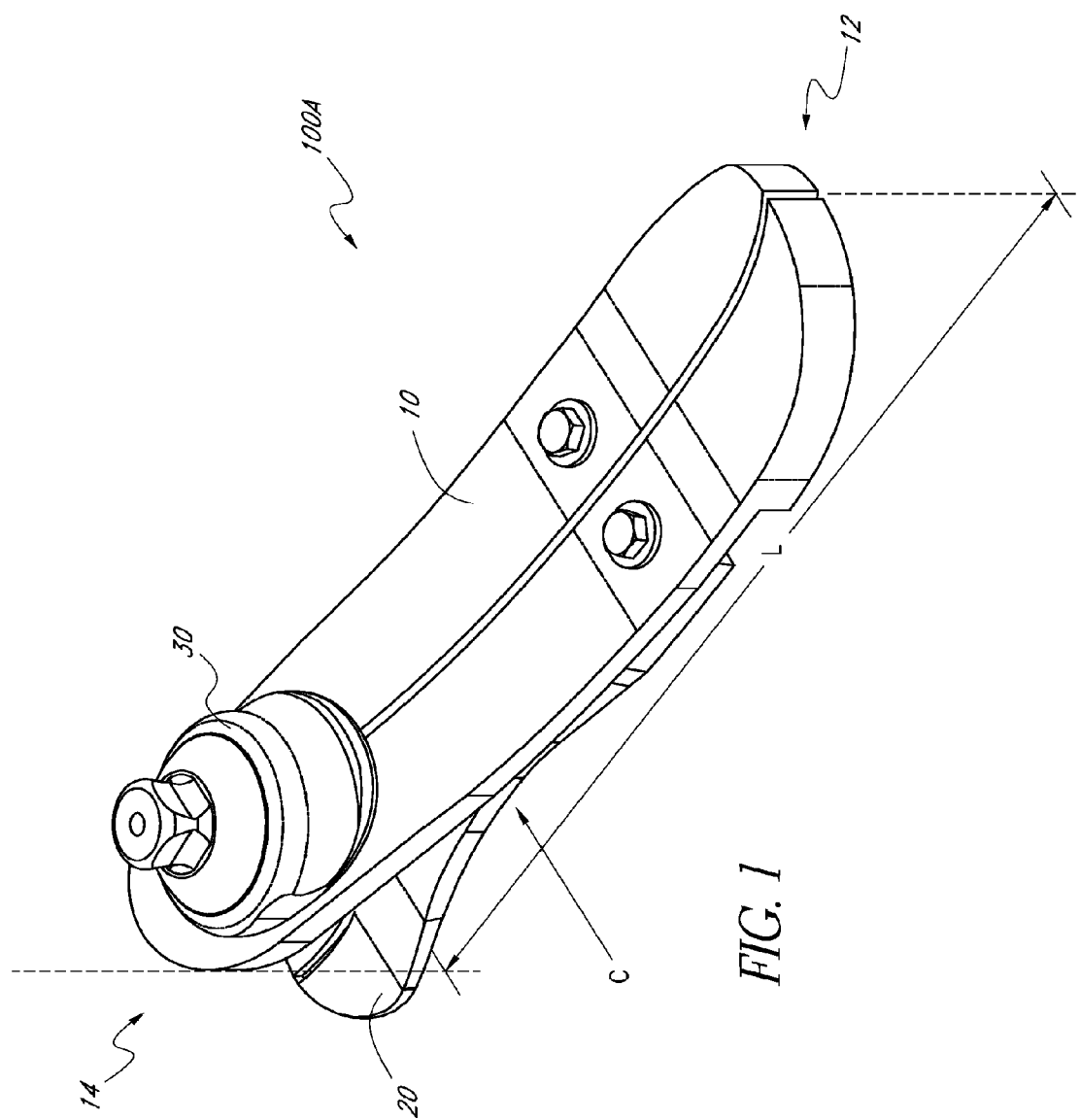
FIG. 1 is a schematic perspective front view of one embodiment of a prosthetic foot.
Figure 2:
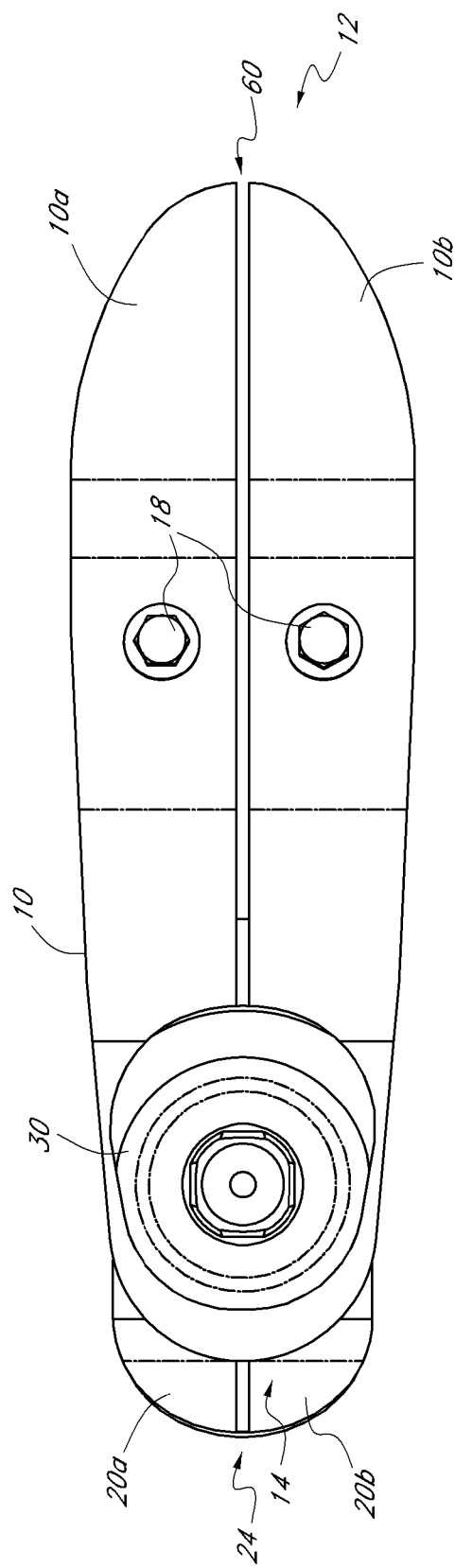
FIG. 2 is a schematic top plan view of the prosthetic foot of FIG. 1
Figure 3:
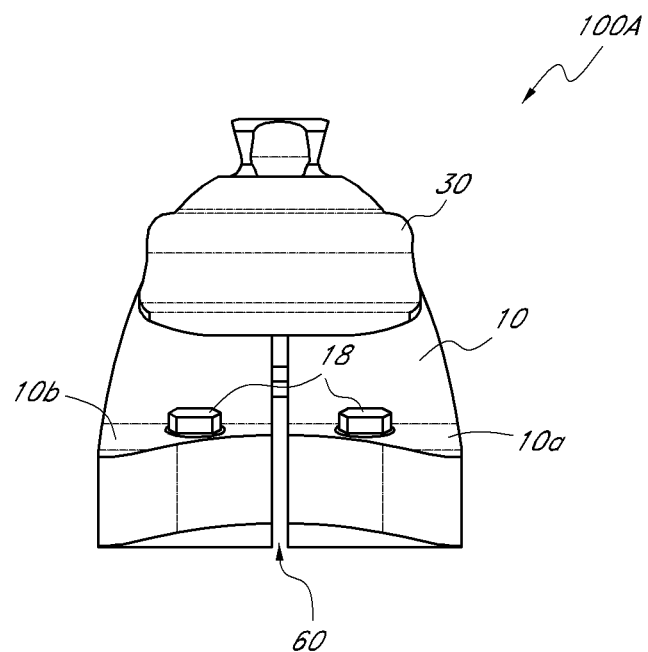
FIG. 3 is a schematic front view of the prosthetic foot of FIG. 1.

FIGS. 1-3 show a prosthetic foot 100A that includes a foot member or support 10 and a heel member or support 20. The prosthetic foot 100A can also have an adapter 30 for removably coupling the prosthetic foot 100A to an amputee (e.g., via a socket or a prosthetic knee). In the illustrated embodiment, the adapter 30 is a pyramid adapter. However, in other embodiments the adapter can have other suitable configurations, such as a tube clamp.

In the illustrated embodiment, the foot member 10 includes two toe members 10a, 10b that extend rearwardly from a front end of the foot member 100A and define a longitudinal slot 60 therebetween. In another embodiment, the foot member can have more than two toe members, with a slot defined between adjacent toe members. In still another embodiment, the foot member can be a single element without a slot defined therein. In another embodiment, the foot member 10 can be substantially flat, and have a substantially rectangular traverse cross-section along its length. In the illustrated embodiment, the prosthetic foot 100A has a plate-like configuration (e.g., the foot 100A can have a foot plate and a heel plate).

In one embodiment, the prosthetic foot 100A can have a length L between a front end 12 and a rear end 14 thereof that generally corresponds to a length of a natural human foot. In one embodiment, the foot member 10 can extend from the rear end 14 to the front end 12 of the prosthetic foot 100A. In another embodiment, the foot member 10 can extend from the rear end 14 of the prosthetic foot 100A to a point rearward of the front end 12 of the prosthetic foot 100A. In still another embodiment the foot member 10 can extend from the front end 12 of the prosthetic foot 100A to a point frontward of the rear end 14 of the prosthetic foot 100A. In still another embodiment, the foot member 10 can extend from a point frontward of the rear end 14 of the prosthetic foot 100A to a point rearward of the front end 12 of the prosthetic foot 100A. In addition, the foot member 10 can comprise multiple pieces separated, for example, transversely or longitudinally from each other. In another embodiment, the foot member 10 may be an integral piece, may be substantially flat, and have a substantially rectangular traverse cross-section along its length L.

With continued reference to FIGS. 1-3, the heel member 20 can have an elongated configuration. In one embodiment, at least a portion of the heel member 20 can extend generally parallel to a portion of the foot member 10. In the illustrated embodiment, the heel member 20 extends rearwardly from a point intermediate the front end 12 and rear end 14 of the prosthetic foot 100A. In another embodiment, the heel member 20 can extend from the front end 12 of the prosthetic foot 100A. In the illustrated embodiment, the heel member 20 can extend rearward of the foot member 10. In another embodiment, a rear end of the heel member 20 can align with a rear end of the foot member 10. In still another embodiment, a front end of the heel member 20 can align with a front end of the foot member 10.

In the illustrated embodiment, the heel member 20 is directly fastened to the foot member 10 via at least one fastener 18, which can be any suitable fastener (e.g., bolts, rivets, adhesives, resilient bands, clamps). In another embodiment, the heel member 20 is operatively coupled to the foot member 10 via an intermediate member (not shown). In still another embodiment, the heel member 20 and foot member 10 can be a single piece.

In the illustrated embodiment, the heel member 20 can have two separate longitudinal segments 20a, 20b that can flex independent of each other during ambulation of the prosthetic foot 100A, wherein the segments 20a, 20b define a slot 24 therebetween. In another embodiment, the heel member 20 can have more than two longitudinal segments with a slot defined between adjacent segments. In still another embodiment, the heel member 20 can be a single segment without a slot defined therein.

In one embodiment, at least a portion of the heel member 20 can be substantially flat and have a substantially rectangular traverse cross-section along its length. The heel member 20 can in one embodiment be a single piece, and can comprise multiple pieces separated, for example, transversely or longitudinally from one another. It will also be appreciated that the heel member 20 can have other configurations to provide heel support and need not have an elongated configuration.

The prosthetic foot 100A includes a curved lengthwise contour that defines an arch C. In the illustrated embodiment, the arch C is defined by the heel member 20. In another embodiment, the arch C can be defined by the foot member 10. In still another embodiment, the arch C can be defined by both the foot member 10 and the heel member 20. In still another embodiment, the prosthetic foot 100A can have a generally flat lengthwise contour.

The prosthetic foot 100A can be manufactured of any suitable materials used in the prosthetics industry, such as polymer impregnated and encapsulated fibrous laminates, e.g. composites including graphite fiber in a high-toughness epoxy thermoset or thermoplastic resin, or any polymer material, carbon fiber and/or fiber glass and polymer material, nylon and polymer material, aramid and a polymer material, synthetic fibers and polymer material, or the like. Further details on prosthetic foot designs that can be used with the embodiments disclosed herein can be found in U.S. Pat. Nos.

5,037,444; 5,181,933; 5,514,185; 5,776,205; 6,071,313; 5,486,209; 5,514,186; 5,593,457; 5,728,176; 6,165,227; 5,976,191; and U.S. Publication Nos. 2005-0038524; 2007-0106395; 2005-0267603 and 2005-0137717, the entire contents of all of which are hereby incorporated by reference and should be considered a part of this specification.

Figure 4A:
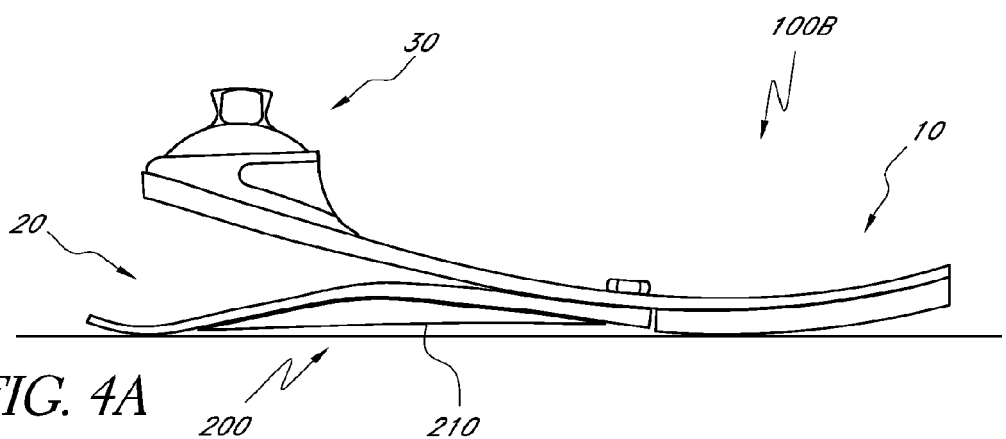
FIGS. 4A-C are schematic side views of the prosthetic foot of FIG. 1 with one embodiment of an insole.
Figure 4B:
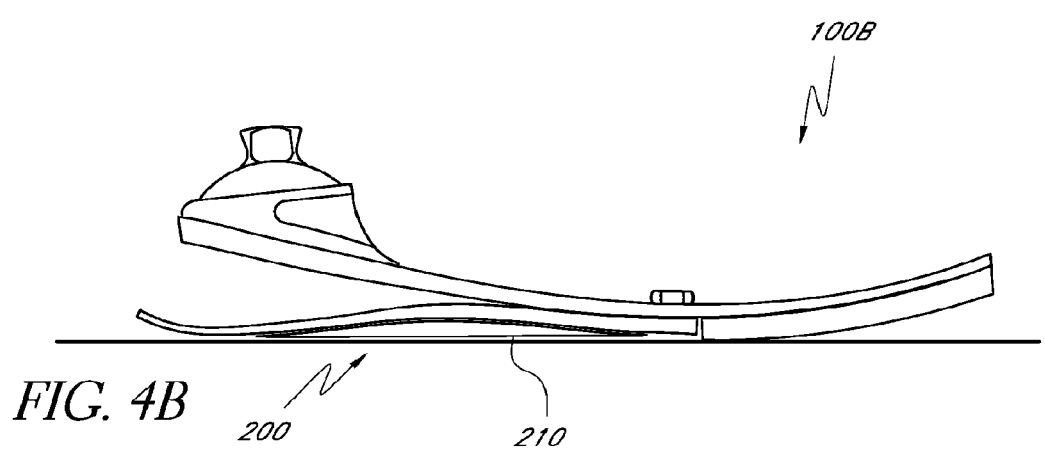
Figure 4C:
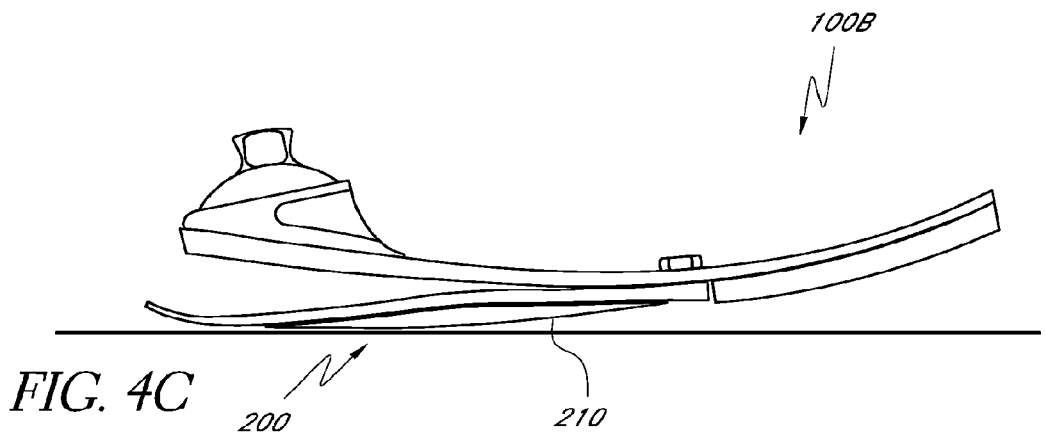

FIGS. 4A-4C show a side view of a prosthetic foot 100B at different stages during ambulation of the prosthetic foot 100B, as further described below. As shown in FIGS. 4A-4B, the prosthetic foot 100B includes an insole member 200 that is disposed in the space defined by the arch C of the prosthetic foot 100A, which in the illustrated embodiment is defined in the heel member 20. However, as noted above, the arch C can be defined in other portions of the prosthetic foot 100 (e.g., in the foot member 10, in the foot and heel members 10, 20).

In one embodiment, the insole member 200 can be fastened to the arch C with an adhesive so that it is fixedly attached to the prosthetic foot 100B. In another embodiment, the insole member 200 can be removably attached to the arch C and can be readily removed to allow for its replacement as desired by a user. In one embodiment, the insole member 200 can include two separate sections, each section attached to one of the heel segments 20a, 20b.

The insole member 200 can, in one embodiment, include a resilient material such as, for example, open cell foam, closed cell foam, urethane, silicone rubber, or any other elastomer. Additionally, the insole member 200 can have a shore density of between about 10 and about 100 Shore A. In another embodiment, the insole member 200 can have a shore density of between about 20 and about 80 Shore A.

In the illustrated embodiment, the insole member 200 defines a generally concave bottom surface 210 when the prosthetic foot is unloaded, as shown in FIG. 4A. With reference to FIG. 4B, the contact surface 210 of the insole member 200 has a generally flat shape relative to the ground when the prosthetic foot 100B is under load and at a standstill position, which advantageously provides increased stability of the prosthetic foot 100B. As shown in FIG. 4C, the contact surface 210 of the insole member 200 is generally convex when the prosthetic foot 100B is loaded at heel-strike and ready for propelling forward. Accordingly, the insole member 200 deforms during a gait cycle so as to provide a smooth progression of the center of mass of the prosthetic foot 100B to thereby provide a rollover performance that approximates the rollover of a natural human foot. However, in other embodiments, the insole member 200 can have other suitable shapes and assume different shapes than those disclosed above during ambulation of the prosthetic foot 100B.

The insole member 200 is preferably sized and shaped to fluidly propel the roll-over of the prosthetic foot 100B during ambulation. The insole member 200 advantageously stores kinetic energy (e.g., from ambulation) at heel strike and returns it in a desired direction with a desired timing. The release phase of the kinetic energy by the insole member 200 preferably starts as soon as the loading phase of the heel 20 has ended at heel strike, which advantageously results in a more stable and more comfortable prosthetic foot 100B.

Advantageously, a greater amount of work is induced at heel strike during ambulation of the prosthetic foot 100B with the insole member 200, resulting in greater bending of the heel member 20, which results in a convex shape of the insole member 200 (see FIG. 4C). This, in turn yields an optimal preloaded roll-over shape, which leads to a smooth, progressive, effortless and more natural gait as the prosthetic foot 100B straightens out (e.g., moves from heel-strike to toe-off).

The insole member 200 advantageously facilitates the guidance of the prosthetic foot's 100B center of mass along a predetermined path as the foot 100B rolls over from heel strike to toe off. For example, the insole member 200 can have at least a first area with a first stiffness and a second area with a second stiffness, where the first stiffness is different from the second stiffness. In other embodiments, the insole member 200 can have more than two areas having a different stiffness. In one embodiment, a stiffness of the prosthetic foot 100B with the insole member 200 can vary in a medial/lateral direction so that the center of mass of the foot 100B can travel toward the medial side of the foot 100B during rollover. For example, the insole member 200 can vary in medial/lateral shape and stiffness so that the center of mass of the prosthetic foot 100B can travel toward the medial side of the foot 100B during rollover. In another example, the medial side of the foot 100B (e.g., medial side of the foot member 10 and/or heel member 20) and/or the insole member 200 can be relatively soft, while the lateral side of the foot 100B and/or the insole member 200 can be relatively stiff. Conversely, to guide the center of mass laterally, the medial side of the foot 100B and/or the insole member 200 can be relatively stiff, while the lateral side of the foot 100B and/or the insole member 200 can be relatively soft.

Those of skill in the art will appreciate that although the insole member 200 can, in one embodiment, have areas of different stiffness or compressibility, other techniques may be used to vary the compressibility of the insole 200. For example, small holes or perforations may be provided in desired locations of the insole member 200. The lack of material at these locations can desirably add to the compressibility or reduced stiffness of the insole member 200. Any such embodiment that provides a varying stiffness to the insole member 200 in desired locations is contemplated. In particular, any embodiment that varies the stiffness of the insole member 200 at particular locations to help guide a desired rollover of the prosthetic foot 100B is contemplated.

Figure 5:
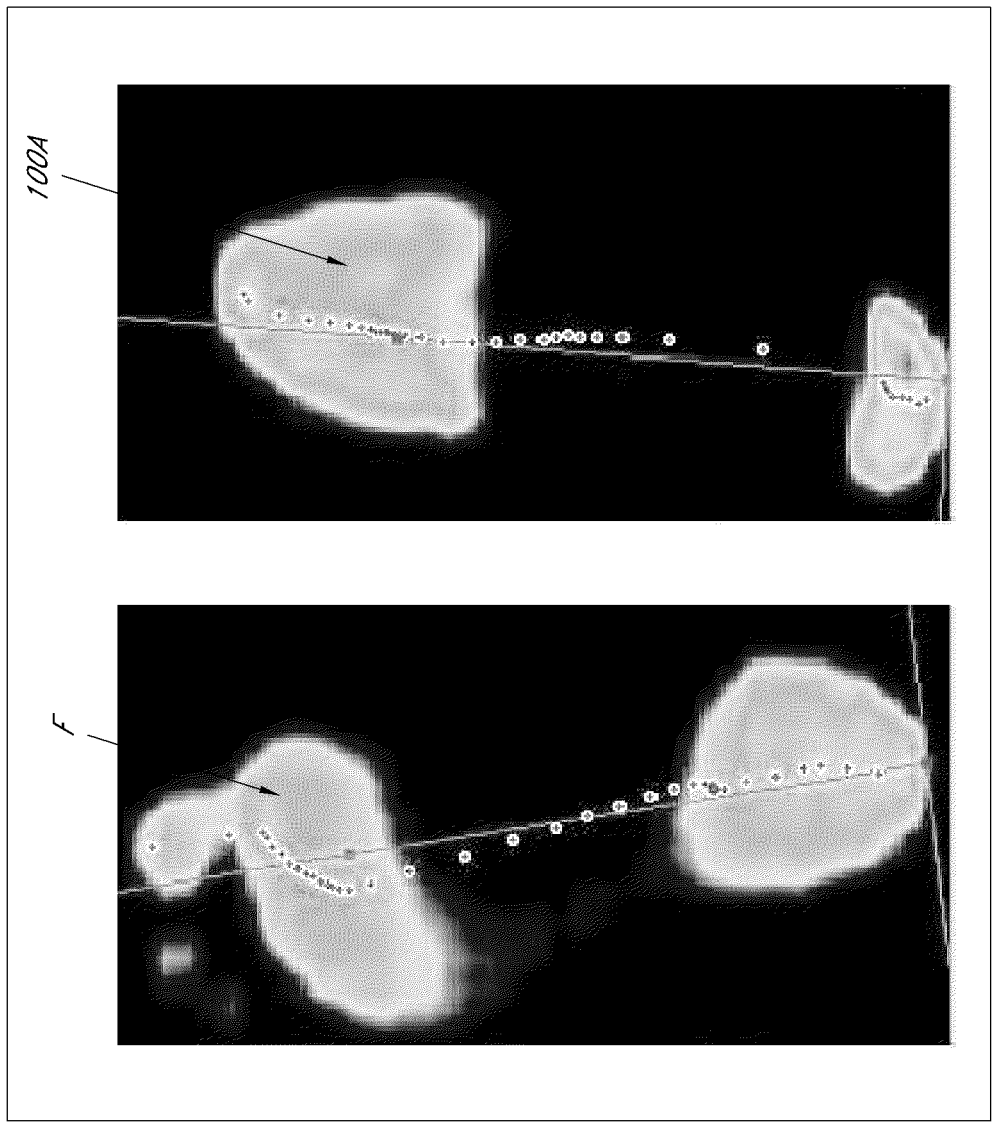
FIG. 5 is a plan view of a scan that maps the movement of the center of pressure of the prosthetic foot of FIGS. 1-3 as the prosthetic foot rolls over from heel strike to toe off, as compared to the rollover of a natural human foot.

FIGS. 5-10 illustrate the advantageous guided rollover that the prosthetic foot 100B achieves. FIG. 5 is a scan of the pressure applied by the prosthetic foot 100A to a walking surface as the prosthetic foot 100A rolls over from heel strike to toe off. The image on the right maps the pressure applied by the prosthetic foot 100A, while the image on the left maps the pressure applied by the wearer's natural left foot F. The dots in each image illustrate the progression of the center of pressure as the prosthetic foot 100A and natural human foot F rollover from heel-strike to toe-off, respectively.

To mimic the path followed by a natural human foot, this center of pressure preferably starts at the center of the heel and travels in a substantially straight line until it reaches approximately the ball of the foot. It then preferably curves medially and continues toward the wearer's first and second toes. Preferably, the distance between each of the dots is substantially uniform, indicating a smooth rollover with no abrupt changes in speed. Further discussion on methods and systems for measuring and illustrating the performance of prosthetic feet, and for designing or modifying prosthetic feet based on said measured performance, can be found in U.S. application Ser. No. 11/184,011, filed Sep. 20, 2004, the entire contents of which are incorporated herein and should be considered a part of this specification.

The scan on the right in FIG. 5, which follows the path of the center of pressure of the prosthetic foot 100A, indicates that there are few dots between heel-strike and the forefoot stance (e.g., mid-stance), while there are many more dots between the mid-stance and toe-off. Moreover, the spacing of the dots between heel-strike and the mid-stance is markedly larger than the spacing of the dots between the mid-stance and toe-off. Moreover, the pressure area at heel-strike is relatively small, which indicates that there is not much flexion of the heel section 20 of the prosthetic foot 100A before the foot 100A moves from heel-strike toward mid-stance. This indicates that the rollover of the prosthetic foot 100A is fast between heel-strike and mid-stance, and relatively slow between mid-stance and toe-off. Such abrupt (non-smooth) rollover performance can result in an unnatural gait that can cause discomfort in an amputee and cause the amputee to expend more effort during ambulation.

Figure 6:
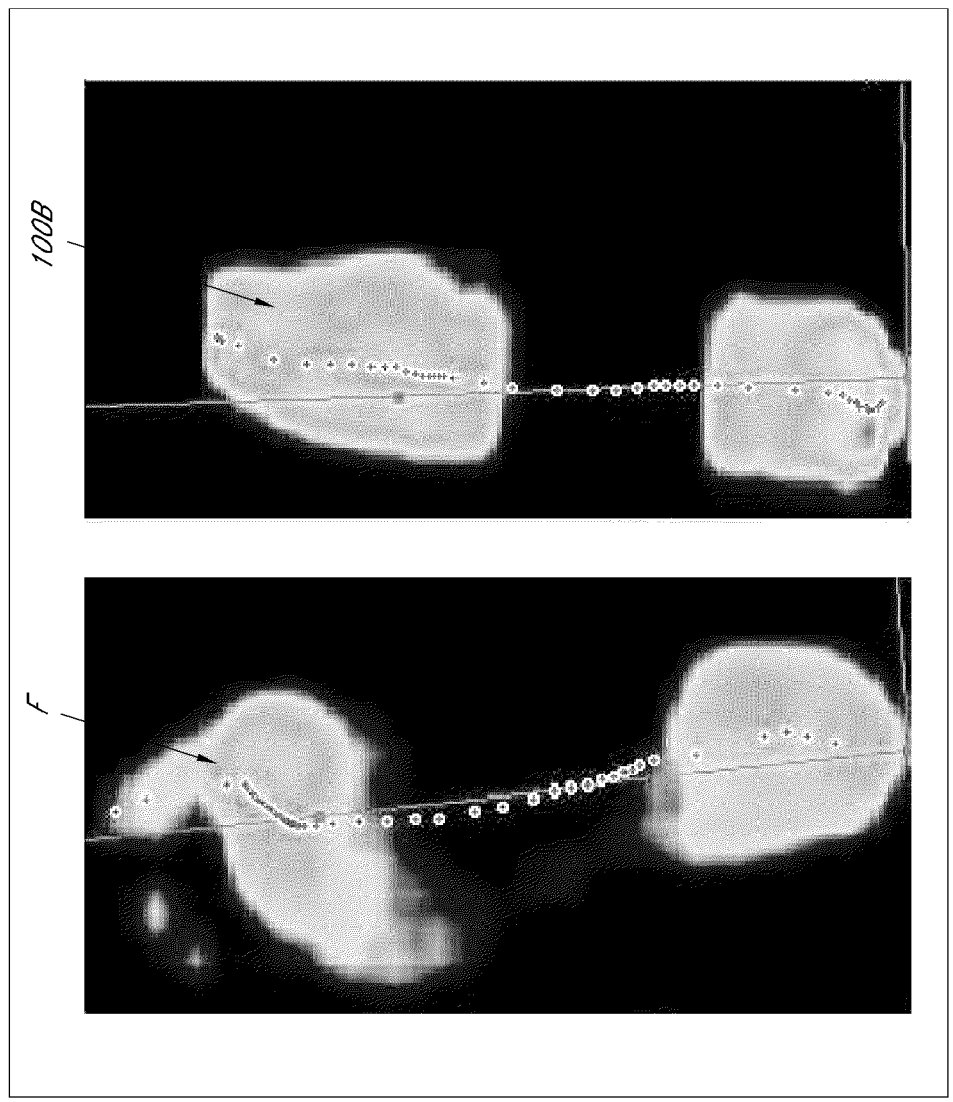
FIG. 6 is a plan view of a scan that maps the movement of the center of pressure of the prosthetic foot of FIGS. 4A-C as the prosthetic foot rolls over from heel strike to toe off, as compared to the rollover of a natural human foot.

FIG. 6 illustrates the performance of the prosthetic foot 100B with the insole member 200, relative to a natural human foot F. The scan on the right in FIG. 6, which follows the path of the center of pressure of the prosthetic foot 100B, indicates a more uniform progression of the center of pressure between heel-strike and mid-stance, as well as a more uniform pressure distribution during mid-stance, as compared to the prosthetic foot 100A in FIG. 5. That is, the dots are substantially uniformly spaced. Moreover, the dots start at the center of the heel and travel in a substantially straight line until they reach approximately the ball of the foot 100B. They then curve medially and continue toward the wearer's first and second toes. Accordingly, the prosthetic foot 100B provides an improved rollover performance. Additionally, the scan in FIG. 6 shows a greater pressure area at heel-strike and toe-off than in FIG. 5, which is representative of a greater amount of work being induced at heel strike, resulting in increased bending of the heel section 20 that results in a more progressive, effortless and natural gait.

Figure 7:
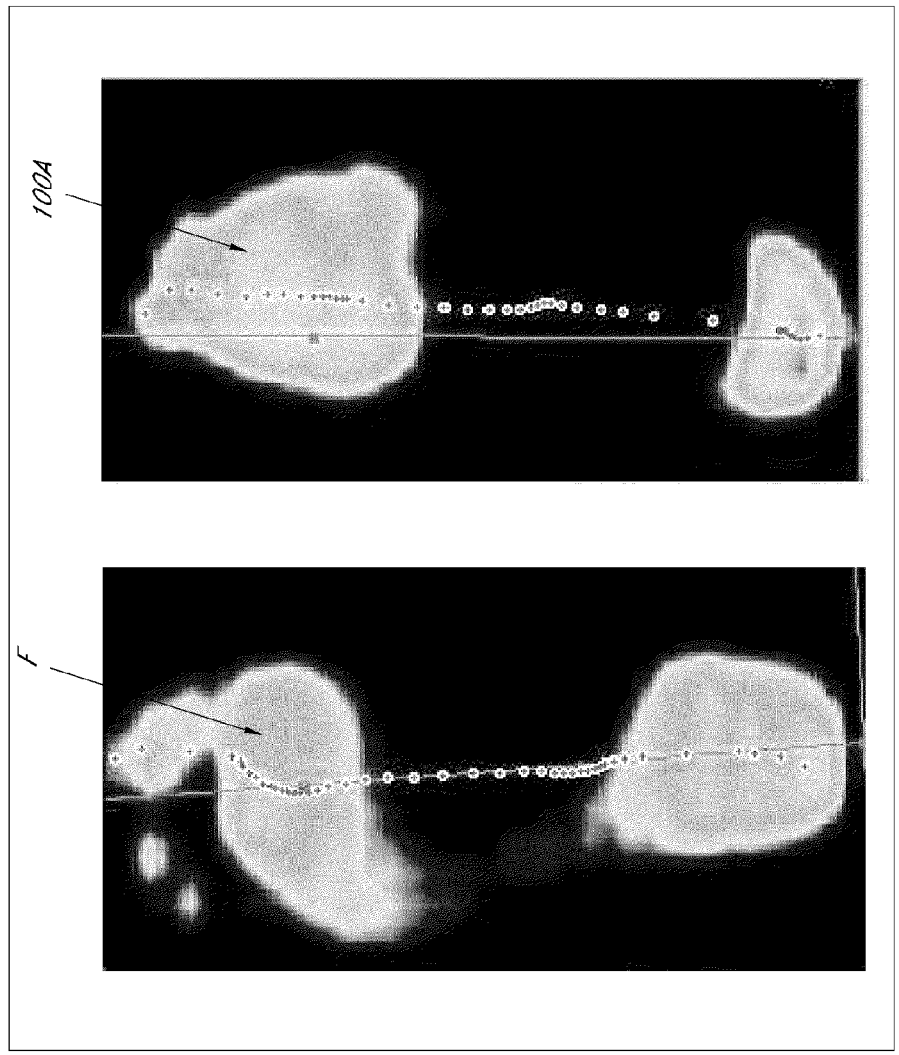
FIG. 7 is a plan view of a scan that maps the movement of the center of pressure of the prosthetic foot of FIGS. 1-3 as the prosthetic foot rolls over from heel strike to toe off, as compared to the rollover of a natural human foot, where a foot cover is disposed over the prosthetic foot.

FIG. 7 shows the performance of the prosthetic foot 100A with a foot cover (not shown) disposed over the prosthetic foot 100A. As shown on the image on the right, many dots are close to each other at mid-stance, which is representative of a dead spot at mid-stance. Such a rollover performance will cause the amputee wearing the prosthetic foot 100A with the foot cover to expend more energy to complete the gait cycle. Again, the pressure area at heel-strike is relatively small, signifying that not much flexion of the heel section 20 occurs at heel strike.

Figure 8:
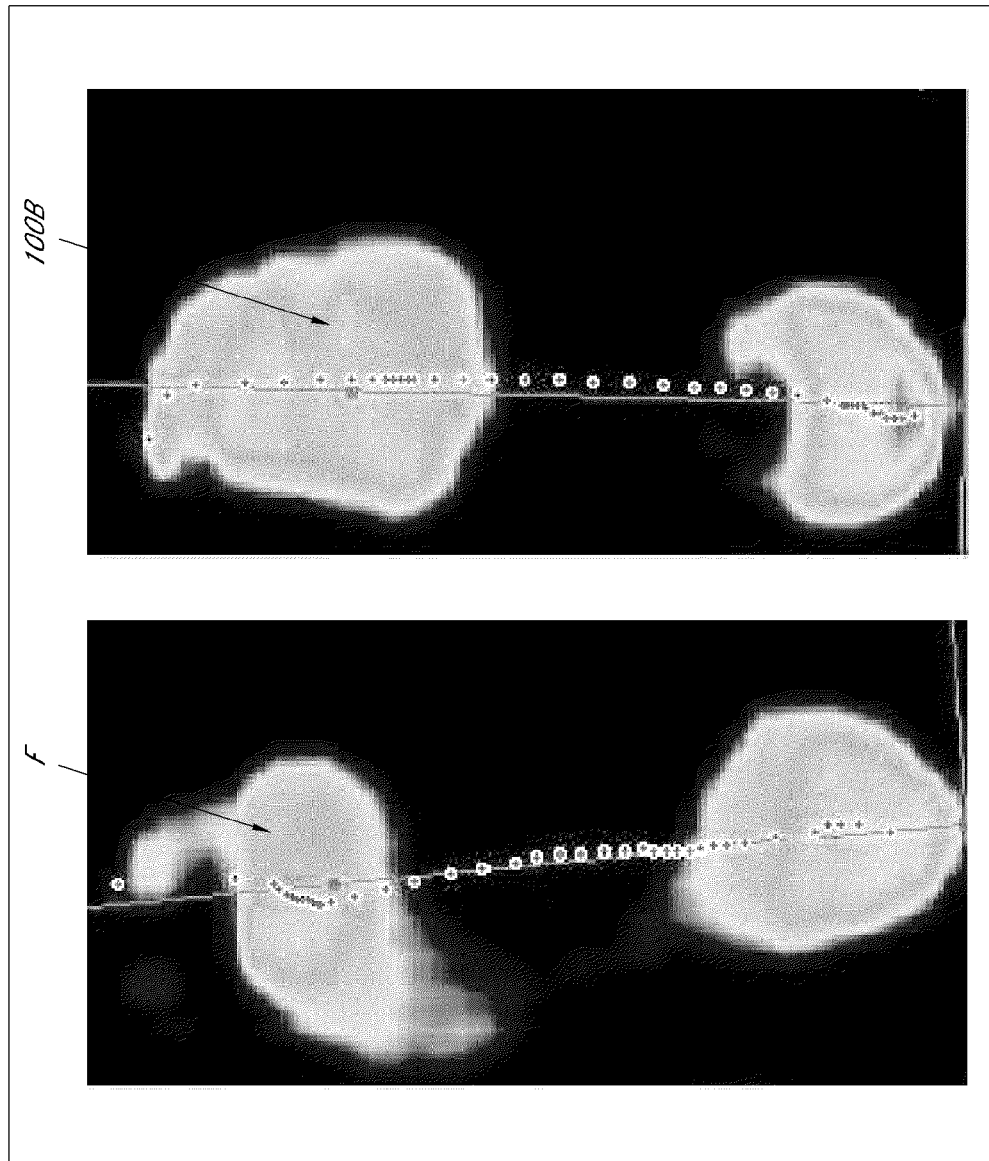
FIG. 8 is a plan view of a scan that maps the movement of the center of pressure of the prosthetic foot of FIGS. 4A-C as the prosthetic foot rolls over from heel strike to toe off, as compared to the rollover of a natural human foot, where a foot cover is disposed over the prosthetic foot.

FIG. 8 shows the performance of the prosthetic foot 100B with a foot cover (not shown) disposed over the prosthetic foot 100B. As shown on the image on the right, the prosthetic foot 100B with the foot cover achieves a more uniform progression of the center of pressure between heel-strike and toe-off, where the dots between heel-strike and toe-off are generally equidistant. Accordingly, the prosthetic foot 100B with the foot cover achieves a smoother rollover performance and a more effortless and natural gait than the prosthetic foot 100A in FIG. 7. Again, the pressure area at heel-strike is larger than in FIG. 7, signifying that more flexion of the heel section 20 occurs at heel strike.

Figure 9:
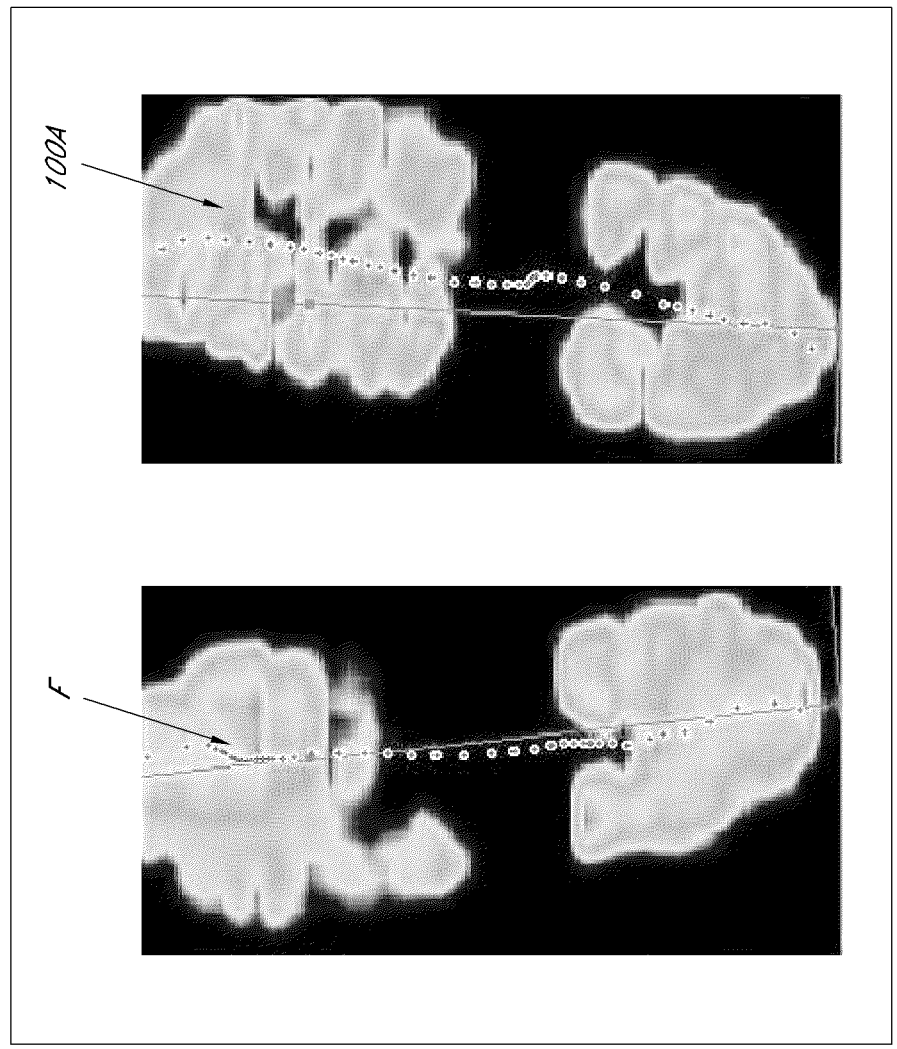
FIG. 9 is a plan view of a scan that maps the movement of the center of pressure of the prosthetic foot of FIGS. 1-3 as the prosthetic foot rolls over from heel strike to toe off, as compared to the rollover of a natural human foot, where a foot cover and shoe is disposed over the prosthetic foot.

FIG. 9 shows the performance of the prosthetic foot 100A with a foot cover (not shown) and shoe (not shown) disposed over the prosthetic foot 100A. As with FIG. 7, the image on the right shows a dead spot at mid-stance (e.g., a lot of dots are shown close together and form a kink in the progression of the center of pressure). Such a rollover performance disadvantageously does not provide a smooth and natural gait.

Figure 10:
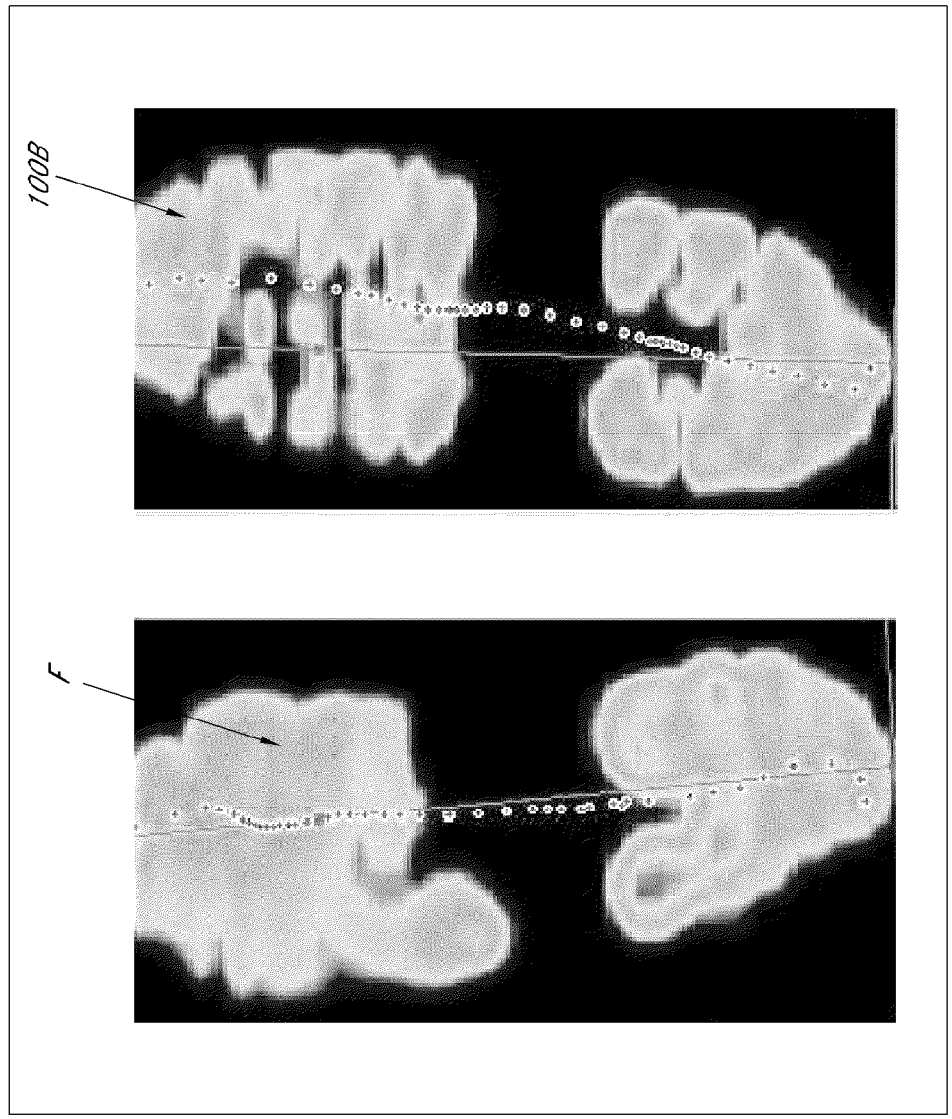
FIG. 10 is a plan view of a scan that maps the movement of the center of pressure of the prosthetic foot of FIGS. 4A-C as the prosthetic foot rolls over from heel strike to toe off, as compared to the rollover of a natural human foot, where a foot cover and shoe is disposed over the prosthetic foot.
Figure 11A:
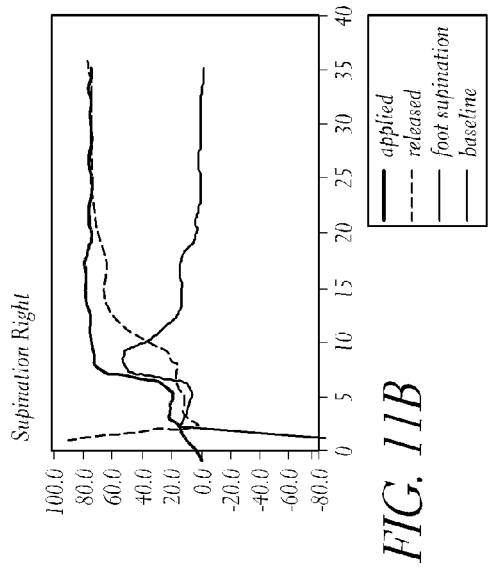
FIGS. 11A-11D are computer screen views of the performance of the natural human foot and prosthetic foot of FIG. 6.
Figure 11B:
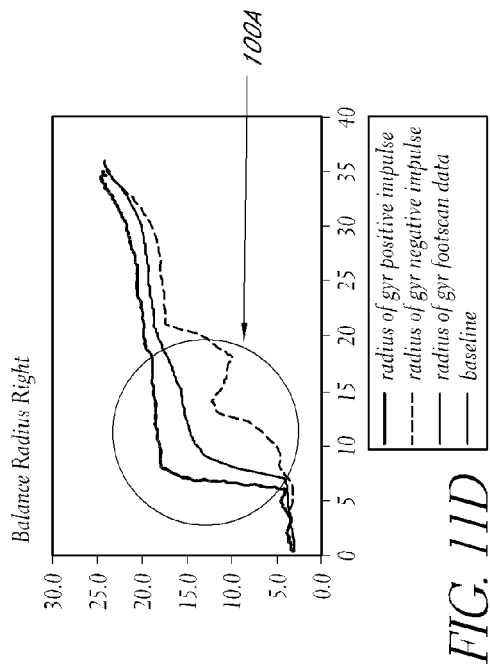
Figure 11C:
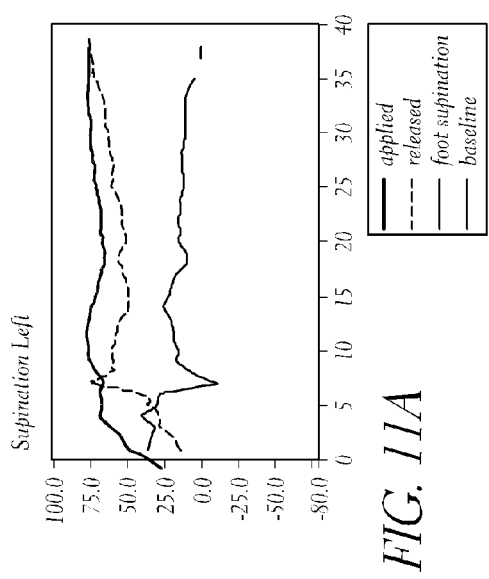
Figure 11D:
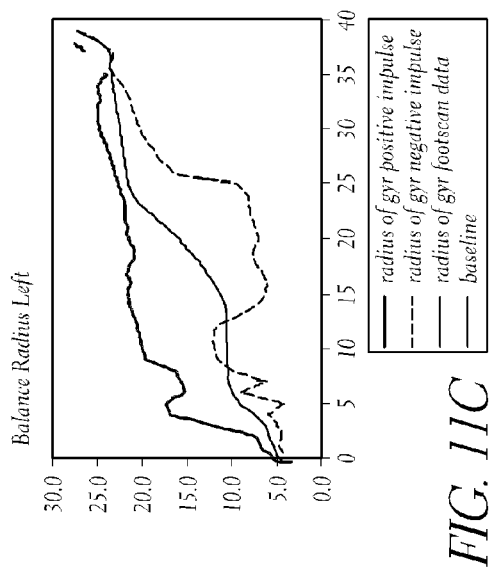
Figure 12A:
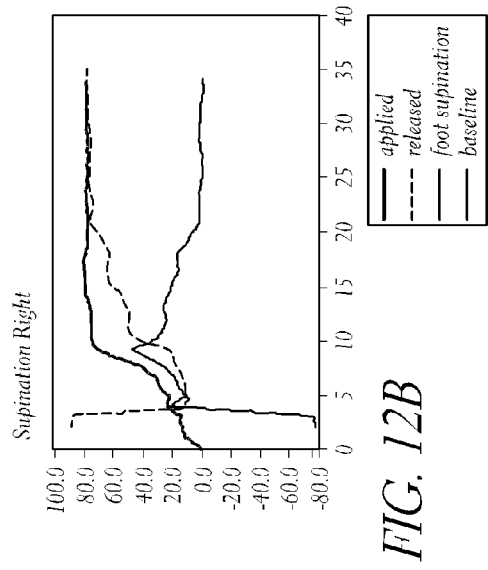
FIGS. 12A-12D are computer screen views of the performance of the natural human foot and prosthetic foot of FIG. 7.
Figure 12B:
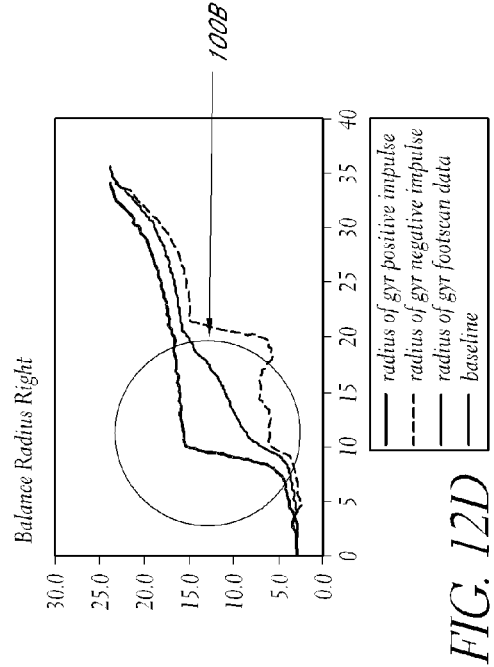
Figure 12C:
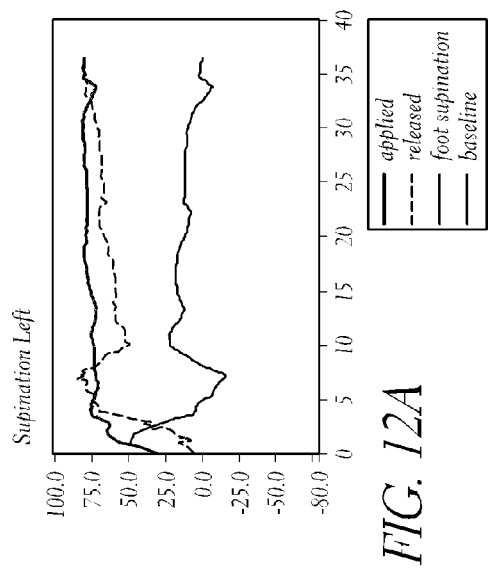
Figure 12D:
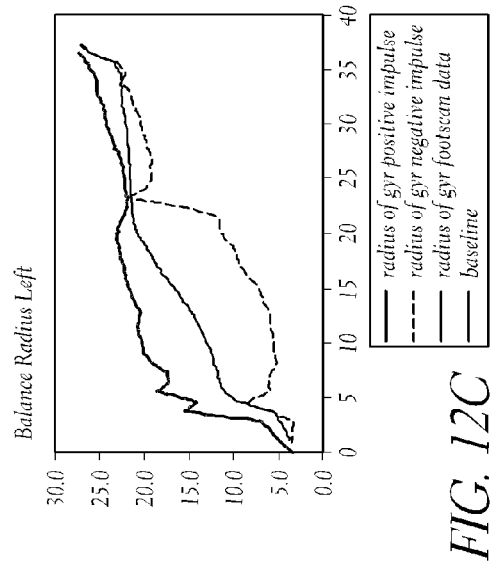

FIG. 10 shows the performance of the prosthetic foot 100B with a foot cover (not shown) and shoe (not shown) disposed over the prosthetic foot 100B. As with FIG. 8, the image on the right shows a more uniform progression of the center of pressure between heel-strike and toe-off than in FIG. 9. Accordingly, the prosthetic foot 100B with the foot cover and shoe also achieves a smoother rollover performance and a more effortless and natural gait than the foot 100A in FIG. 9.

FIGS. 11A-11D and 12A-12D show graphs representing the performance of the prosthetic feet 100A, 100B relative to the natural human foot F. The graphs on the upper left (FIGS. 11A, 12A) illustrate the supination performance of the natural human foot F. The graphs on the lower left (FIGS. 11C, 12C) illustrate the balance radius performance of the natural human foot F. The graphs on the upper right (FIGS. 11B, 12B) show the supination performance of the prosthetic feet 100A, 100B. The graphs on the lower right (FIGS. 11D, 12D) show the balance radius performance of the prosthetic feet 100A, 100B.

In FIGS. 11A-11D, the graphs on the right-hand side (FIGS. 11B, 11D) show the performance of the prosthetic foot 100A. With respect to the balance radius graph (lower right-hand side—FIG. 11D), the middle curve is a graph of the distance between the center of pressure of the prosthetic foot 100A during ambulation (e.g., as shown in FIG. 5). As shown in the circled area in FIG. 11D, the middle curve has a generally box shape, which signifies an undesirable rollover performance.

In FIGS. 12A-12D, the graphs on the right-hand side (FIGS. 12B, 12D) show the performance of the prosthetic foot 100B. With respect to the balance radius graph (lower right-hand side—FIG. 12D), the middle curve (e.g., within the circled area) has a more uniform linear shape that approximates the shape of the middle curve in the balance radius graph for the natural human foot F. Accordingly, the prosthetic foot 100B exhibits a more smooth and natural gait (e.g., as shown in FIG. 6).

Figure 13:
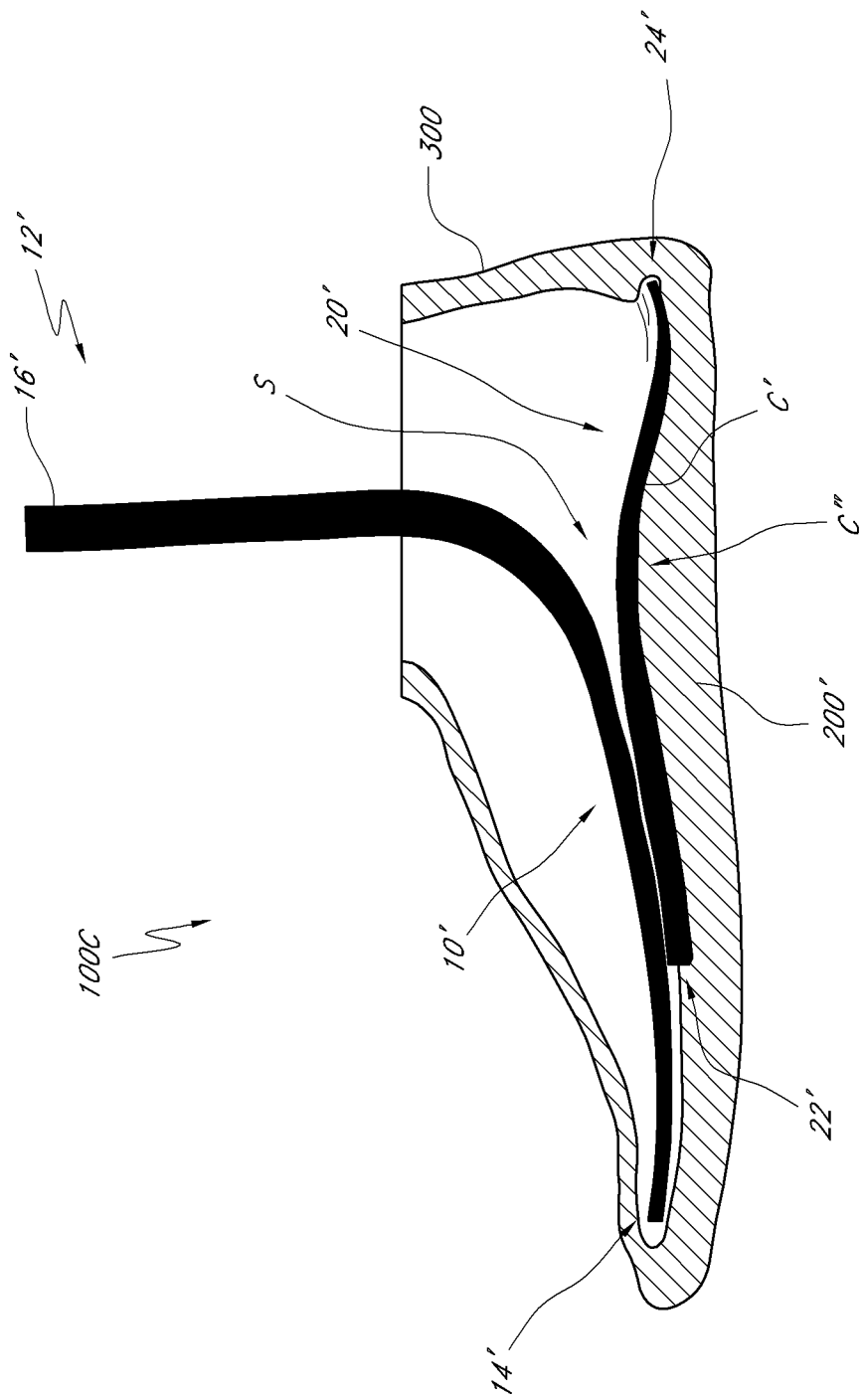
FIG. 13 is a cross-sectional side-view of another embodiment of a prosthetic foot with an insole portion.

FIG. 13 shows another embodiment of a prosthetic foot 100C. The prosthetic foot 100C can include a foot member 10' extending from a proximal end 12' to a distal end 14'. In one embodiment, the proximal end 12' corresponds to an attachment portion 16' for coupling the prosthetic foot 100C to another prosthetic component, such as a pylon or socket. In one embodiment, the distal end 14' of the foot member 10' coincides with a toe portion of a natural human foot. In another embodiment, the distal end 14' coincides with a portion disposed proximal of the toes of a natural human foot.

The prosthetic foot 100C can also include a heel member 20' extending from a proximal end 22' to a distal end 24'. In one embodiment, the distal end 24' extends distally of the foot member 10' and defines a slot S between the heel member 20' and the foot member 10'. In one embodiment, the proximal end 22' of the heel member 20' can extend generally parallel to the foot member 10'. The heel member 20' can be attached to the foot member 10'. In another embodiment, the heel member and foot member can be integrally formed.

The prosthetic foot 100C can also include a foot cover 300 (see FIGS. 13 and 14A) removably coupleable to one or both of the foot member 10' and heel member 20'. In the illustrated embodiment, the foot cover 300 can incorporate an insole portion 200', similar to the insole portion 200 described above. In the illustrated embodiment, the insole portion 200' is integrally formed with the foot cover 300. As shown in FIG. 13, the insole portion 200' of the foot cover 300 can contact one or both of the heel member 20' and foot member 10'. In a preferred embodiment, the insole member 200' can include a contour C" that contacts a similarly contoured surface C' of the heel member 20' and foot member 10'. In one embodiment, the contours C', C" are arched contours. In another embodiment, the contours C', C" can be generally flat contours. In one embodiment, the insole member 200' is attached to one or both of the foot member 10' and heel member 20' so that the insole member 200' is in constant contact with the foot member 10' and/or heel member 20' during ambulation of the prosthetic foot 100C. Further information on foot covers can be found in U.S. application Ser. No. 11/139,009, filed May 26, 2005, the entire contents of which are hereby incorporated by reference and should be considered a part of this specification.

Advantageously, the insole portion 200' deforms during a gait cycle of the prosthetic foot 100C so as to provide a smooth progression of the center of mass of the prosthetic foot 100C to thereby provide a rollover performance that approximates the rollover of a natural human foot. Advantageously, the insole member 200, 200' maintains a generally continuous contact between the heel member 20, 20' (and/or foot member 10, 10') with the support surface (e.g., floor) from at least heel-strike to mid-stance during ambulation of the prosthetic foot 100B, 100C. In one embodiment, the insole member 200' has a generally planar surface 210' that extends, for example, from the distal end of the foot cover 300 to approximately a metatarsal portion of the foot cover 300. The insole portion 200' is preferably sized and shaped to fluidly propel the roll-over of the prosthetic foot 100C during ambulation. During ambulation, the insole portion 200' advantageously stores kinetic energy at heel strike and returns it in a desired direction with a desired timing in subsequent gait phases, such as mid-stance and toe-off. The release phase of the kinetic energy by the insole portion 200' preferably starts as soon as the loading phase of the heel member 20' has ended at heel strike, which advantageously results in a more stable and more comfortable prosthetic foot 100C.

Advantageously, a greater amount of work is induced at heel strike during ambulation of the prosthetic foot 100C with the insole portion 200', resulting in greater bending of the heel member 20'. This, in turn yields an optimal preloaded roll-over shape, which leads to a smooth, progressive, effortless and more natural gait as the prosthetic foot 100C straightens out (e.g., moves from heel-strike to toe-off), thereby avoiding an interruption or slowing down of rollover between heel strike of the foot 100C and mid-stance.

The insole portion 200' advantageously facilitates the guidance of the prosthetic foot's 100C center of mass along a predetermined path as the foot 100C rolls over from heel strike to toe-off. For example, the insole portion 200' can have at least a first area with a first stiffness and a second area with a second stiffness, where the first stiffness is different from the second stiffness. In other embodiments, the insole portion 200' can have more than two areas having a different stiffness.

Figure 14A:
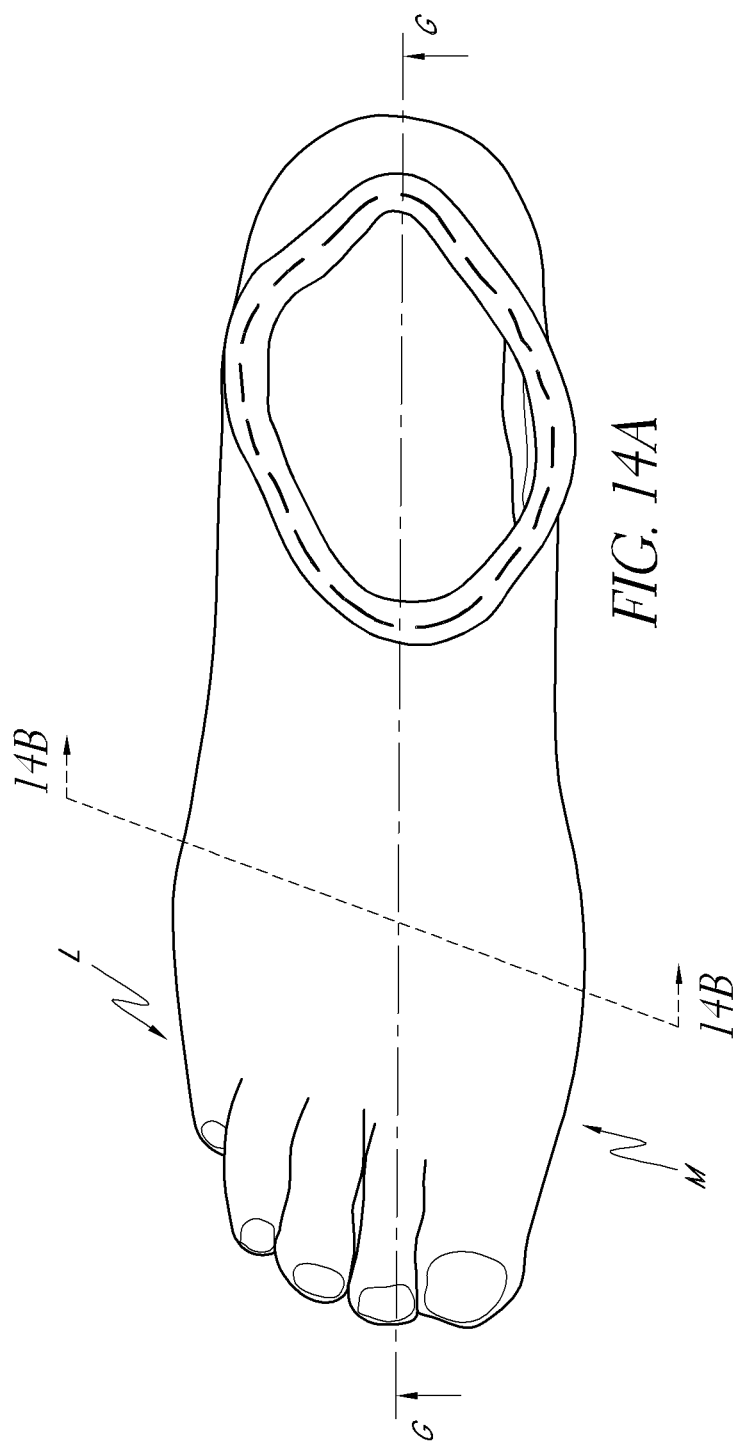
FIG. 14A is a top view of the foot-cover of the prosthetic foot in FIG. 13.
Figure 14B:
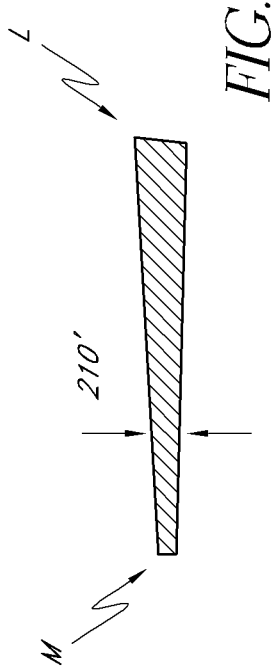
FIG. 14B is a cross-sectional transverse view of the foot cover of FIG. 14A along line 14B-14B.

In one embodiment, a stiffness of the prosthetic foot 100C with the insole member 200' can vary in a medial/lateral direction so that the center of mass of the foot 100C can travel toward the medial side of the foot 100C during rollover. For example, in one embodiment the insole portion 200' can vary in thickness 210' along the anterior-posterior direction of the foot cover 300, as shown in FIG. 13. Additionally, in one embodiment, the insole portion 200' can vary in thickness 210' in the medial-lateral direction from a medial side M to a lateral side L, as shown in FIGS. 14A-14B. In the illustrated embodiment, the insole portion 200' of the foot cover 300 has a transverse cross-section with a greater thickness 210' at the lateral side L than at the medial side M, so that the center of mass of the prosthetic foot 100C can be guided toward the medial side M of the foot 100C during ambulation of the prosthetic foot 100C. In a preferred embodiment, the difference in thickness 210' between the lateral side L and the medial side M can be between about 1.2 mm and about 2 mm. However, in other embodiments, the difference in thickness 210' between the lateral side L and the medial side M can be less than about 1.2 mm or greater than about 2 mm. In one embodiment, the thickness 210' of the medial side M can differ from the thickness 210' of the lateral side L at a desired section of the prosthetic foot 100C (e.g., the thickness 210' can vary at the metatarsal section of the prosthetic foot 100C). In another embodiment, the thickness 210' of the medial side M can differ from the thickness 210' of the lateral side L at more than one section along the length of the prosthetic foot 100C. In still another embodiment, the thickness 210' of the medial side M can differ from the thickness 210' of the lateral side L along the entire length of the prosthetic foot 100C.

In another example, the medial side M of the foot member 10' and/or heel member 20', and/or the medial side M of the insole portion 200' can be relatively soft, while the lateral side L of the foot member 10' and/or heel member 20', and/or the lateral side L of the insole portion 200' can be relatively stiff. Conversely, in another embodiment, to guide the center of mass laterally, the medial side M of the foot member 10' and/or heel member 20', and/or the medial M side of the insole portion 200' can be relatively stiff, while the lateral side L of the foot member 10' and/or heel member 20', and/or the lateral side L of the insole portion 200' can be relatively soft.

Figure 15C:
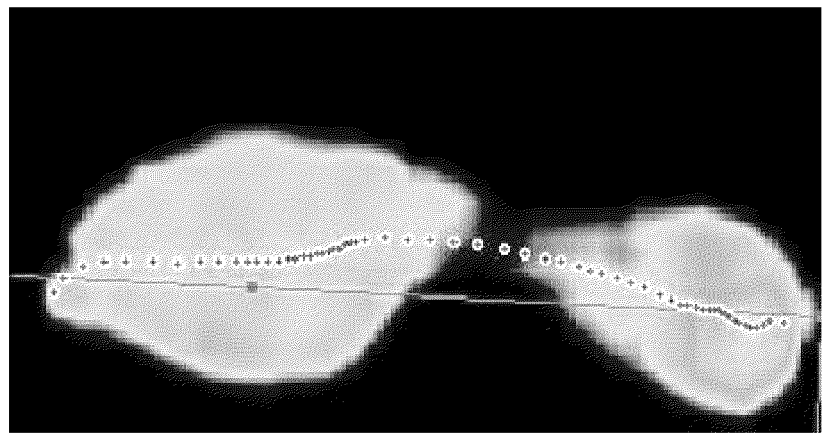
FIG. 15C is a plan view of a scan that maps the movement of the center of pressure of the prosthetic foot 100C of FIG. 13 with the foot cover of FIGS. 14A-14B as the prosthetic foot rolls over from heel strike to toe off.
Figure 15B:
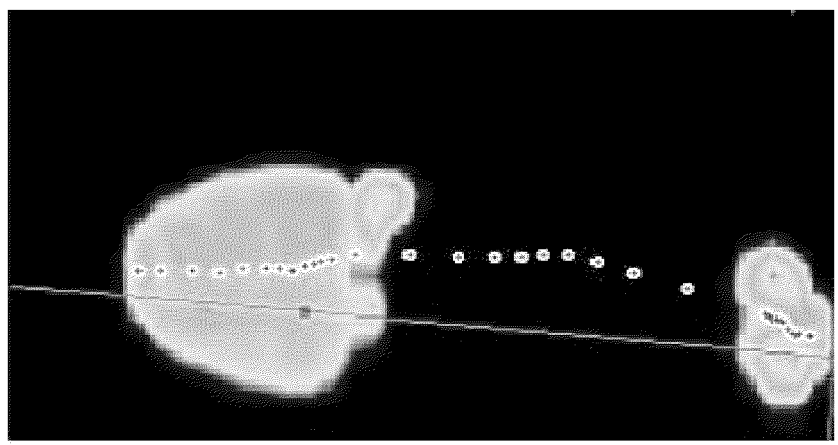
FIG. 15B is a plan view of a scan that maps the movement of the center of pressure of the prosthetic foot of FIGS. 1-3 with a conventional foot cover.
Figure 15A:
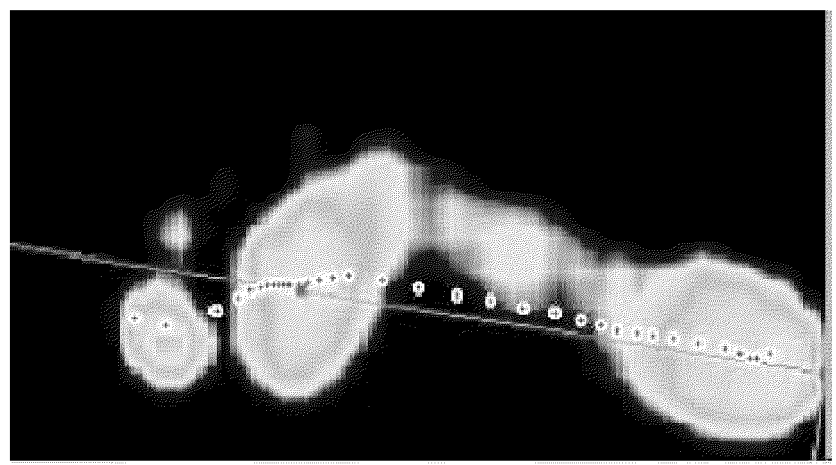
FIG. 15A is a plan view of a scan that maps the movement of the center of pressure of an abled bodied human foot.

FIG. 15A illustrates the rollover performance of natural human foot. In the illustrated embodiment, the scan shows the rollover of a right foot from heel-strike to toe-off. As can be seen in FIG. 15A, the progression of the center of pressure (as represented by the dots) is generally uniform (e.g., the dots are generally evenly spaced) from heel-strike to mid-stance and trend toward the medial side as the foot moves from mid-stance to toe-off.

FIG. 15B illustrates the rollover performance of the prosthetic foot 100A with a conventional foot cover. As shown on in FIG. 15B, the spacing between the dots (which represent the progression of the center of pressure of the prosthetic foot) is not uniform between heel-strike and mid-stance, which is representative of a non-smooth rollover performance of the prosthetic foot 100A. Additionally, the spacing of the dots is greater just after heel-strike and then decreases as rollover continues toward mid-stance, which is representative of a dead spot at mid-stance (i.e., there is a slowdown in rollover at mid-stance). Such a rollover performance will cause the amputee wearing the prosthetic foot to expend more energy to complete the gait cycle. The pressure indication at heel-strike is relatively small, signifying that not much flexion of the heel section 20 occurs at heel strike and that the prosthetic foot 100A transitions from heel-strike toward mid-stance relatively quickly, before the rollover slows down, as discussed above.

FIG. 15C illustrates the performance of the prosthetic foot 100C with the foot cover 300 having the insole member 200', which provides an improved rollover performance than the performance illustrated in FIG. 15B. As illustrated in FIG. 15C, the progression of the center of pressure is generally uniform (e.g., evenly spaced dots) between heel-strike and mid-stance, which is representative of a relatively smoother rollover performance of the prosthetic foot 100C, as compared to the rollover performance of the prosthetic foot 100A in FIG. 15B. Additionally, the pressure indication at heel-strike is larger, with a greater number of dots at heel-strike, which is representative of increased flexion of the heel section 20' at heel-strike, as compared to the rollover performance in FIG. 15B. Accordingly, the rollover performance of the prosthetic foot 100C in FIG. 15C more closely approximates the rollover performance of the natural human foot of an abled bodied individual, shown in FIG. 15A.

Figure 16:
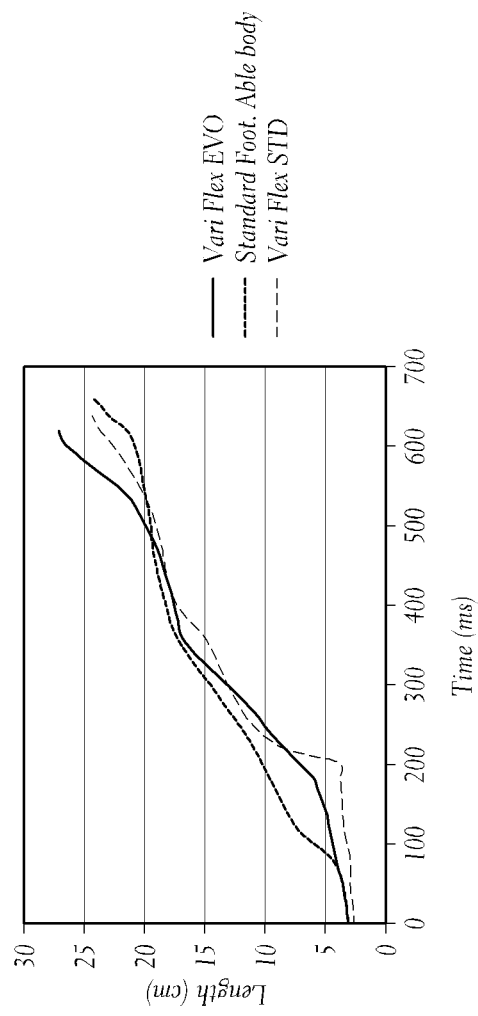
FIG. 16 is a graph comparing the rollover performance of the natural human foot and prosthetic feet in FIGS. 15A-15C.
Figure 17:
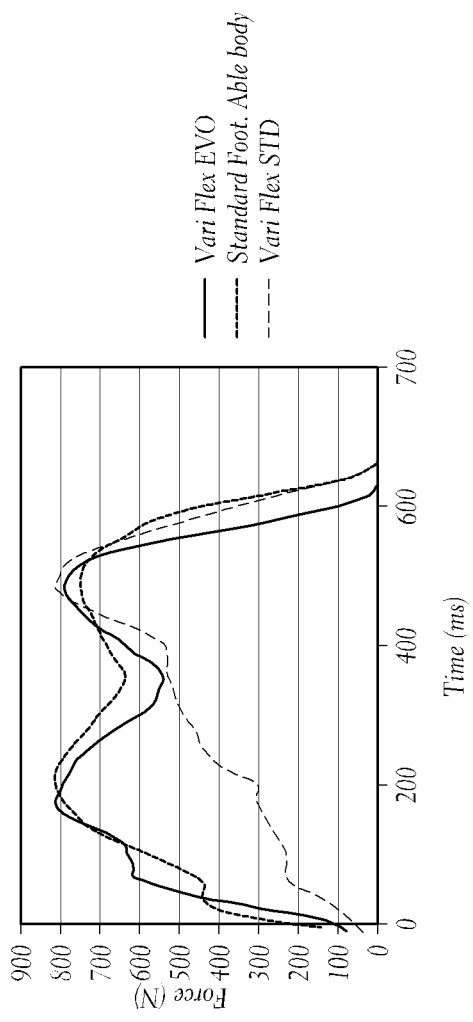
FIG. 17 is another graph comparing the rollover performance of the natural human foot and prosthetic feet in FIGS. 15A-15C.

FIGS. 16 and 17 show graphs representing the performance of the natural human foot in FIG. 15A, prosthetic feet 100A in FIG. 15B, and prosthetic foot 100C in FIG. 15C. FIG. 16 shows a graph of the balance radius performance. As can be seen in FIG. 16, the lightest hued line illustrates a graph of the distance between the center of pressure of the prosthetic foot 100A during ambulation, the middle hued line illustrates a graph of the distance between the center of pressure of the prosthetic foot 100C during ambulation, and the darkest hued line illustrates a graph of the distance between the center of pressure of the natural human foot during ambulation. The curves for the prosthetic foot 100C more closely approximates the curve for the natural human foot. Additionally, the curve for the prosthetic foot 100A has a generally box shape with an inflection point occurring at about 200 ms, which signifies an undesirable rollover performance.

FIG. 17 shows a comparison of the vertical ground reaction force of the natural human foot in FIG. 15A (darkest hued line), prosthetic feet 100A in FIG. 15B (lightest hued line), and prosthetic foot 100C in FIG. 15C (middle hued line). As can be seen in FIG. 17, the line for the prosthetic foot 100C more closely approximates the performance of the natural human foot, which shows that the prosthetic foot 100C more closely approximates the rollover performance of the natural human foot.

Although these inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. For example, steps of the method(s) disclosed herein can be performed in an order other than that disclosed in the illustrated embodiments, and additional, fewer, or different steps may be performed and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above.

What is claimed is:

1. A prosthetic foot, comprising:
   a foot member having an upper surface and a lower surface, the lower surface defining a concave contoured arch portion that faces a support surface that the prosthetic foot contacts during use, the foot member comprising an elongate plate extending in a posterior to anterior direction from a rear end to a front end; and
   a foot cover configured to receive and contact the foot member therein, the foot cover comprising an upper opening and an interior volume defining an upper interior surface, the foot member being insertable through said upper opening into said interior volume, wherein insertion of the foot member into the foot cover through the upper opening places the lower surface of the foot member into contact with the upper interior surface, the upper interior surface configured to contact the lower surface of the foot member over an entire length of the concave contoured arch portion when the lower surface of the foot member is placed into contact with the upper interior surface and during ambulation of the prosthetic foot, the upper interior surface having an upper convex surface, wherein the upper convex surface is curved over the entire length of the upper convex surface and corresponds in shape with the concave contoured arch portion of the foot member, the upper interior surface configured to facilitate a rollover of the prosthetic foot in at least one of a lateral-medial and medial-lateral direction during ambulation;
   wherein the concave contoured arch portion is defined between anterior and posterior inflection points beyond which the lower surface is no longer concave, the lower surface gradually transitioning from the concave contoured arch portion to a convex contoured heel section posterior to the concave contoured arch portion and the upper interior surface configured to contact the entire arch portion from the anterior inflection point to the posterior inflection point.

2. The prosthetic foot of claim 1, wherein the upper interior surface is configured to maintain the foot member in continuous contact with the support surface from at least a heel-strike position to a mid-stance position during ambulation of the prosthetic foot to provide a substantially uniform progression of a center of pressure of the foot from heel-strike to mid-stance and a substantially smooth rollover.

3. The prosthetic foot of claim 1, wherein the foot member comprises a foot plate and a heel plate operatively coupled to the foot plate, the foot plate and the heel plate comprising discrete members.

4. The prosthetic foot of claim 3, wherein the heel plate comprises the concave contoured arch portion.

5. The prosthetic foot of claim 1, the upper interior surface having variable thickness in a medial-lateral direction to facilitate the rollover of the prosthetic foot in at least one of a lateral-medial and medial-lateral direction during ambulation.

6. The prosthetic foot of claim 1, wherein the foot cover is configured to removably receive the foot member.

7. The prosthetic foot of claim 1, wherein the foot cover is made of an elastomeric material.

8. A prosthetic foot, comprising:
   a body generally shaped like a natural human foot defining a cavity having an upper opening and an upper interior surface therein configured to removably receive a prosthetic foot member, wherein the body is made of an elastomeric material;
   a prosthetic foot member having an elongate plate-like configuration, the prosthetic foot member having an upper surface and a lower surface, the lower surface defining a concave contoured arch portion that faces a support surface that the prosthetic foot contacts during use; and
   an insole member provided along the upper interior surface, the insole member configured to be in constant contact with the foot member over an entire length of the concave contoured arch portion and having an upper convex surface, wherein the upper convex surface is curved over the entire length of the upper convex surface and corresponds in shape with the concave contoured arch portion of the foot member, the insole member comprising a first section having a first stiffness and a second section having a second stiffness different than the first stiffness to facilitate a rollover of the prosthetic foot in at least one of a lateral-medial and medial-lateral direction during ambulation;
   wherein the concave contoured arch portion is defined between anterior and posterior inflection points beyond which the lower surface is no longer concave, the lower surface gradually transitioning from the concave contoured arch portion to a convex contoured heel section posterior to the concave contoured arch portion and the insole member configured to contact the entire arch portion from the anterior inflection point to the posterior inflection point.

9. The prosthetic foot of claim 8, wherein the insole member is integral with the body.

10. The prosthetic foot of claim 8, wherein the insole member is configured to maintain the prosthetic foot member in continuous contact with the support surface from at least a heel-strike position to a mid-stance position during ambulation of the prosthetic foot to provide a substantially uniform progression of a center of pressure of the foot from heel-strike to mid-stance and a substantially smooth rollover.

11. The prosthetic foot of claim 8, wherein the first section having the first stiffness has a first thickness and the second section having the second stiffness has a second thickness less than the first thickness.

12. The prosthetic foot of claim 8, wherein the insole member is made of a foam material.

13. The prosthetic foot of claim 8, wherein the foot member comprises a foot plate and a heel plate operatively coupled to the foot plate, the foot plate and the heel plate comprising discrete members.

14. The prosthetic foot of claim 13, wherein the heel plate comprises the concave contoured arch portion.

15. A prosthetic foot, comprising:
a foot member having an upper surface and a lower surface, the lower surface defining a concave contoured arch portion that faces a support surface that the prosthetic foot contacts during use, the foot member comprising an elongate plate extending in a posterior to anterior direction from a rear end to a front end; and
a foot cover configured to removably receive and contact the foot member therein, the foot cover comprising an upper opening and an interior volume defining an upper interior surface, the foot member being insertable through said upper opening into said interior volume, wherein insertion of the foot member into the foot cover through the upper opening places the lower surface of the foot member into contact with the upper interior surface, the upper interior surface configured to be in continuous contact with the lower surface of the foot member over an entire length of the concave contoured arch portion when the lower surface of the foot member is placed into contact with the upper interior surface and during ambulation of the prosthetic foot, the upper interior surface having an upper convex surface, wherein the upper convex surface is curved over the entire length of the upper convex surface and corresponds in shape with the concave contoured arch portion of the foot member, the upper interior surface having variable thickness in a medial-lateral direction to facilitate a rollover of the prosthetic foot in at least one of a lateral-medial and medial-lateral direction during ambulation;
wherein the concave contoured arch portion is defined between anterior and posterior inflection points beyond which the lower surface is no longer concave, the lower surface gradually transitioning from the concave contoured arch portion to a convex contoured heel section posterior to the concave contoured arch portion and the upper interior surface configured to contact the entire arch portion from the anterior inflection point to the posterior inflection point.

16. The prosthetic foot of claim 15, wherein the upper interior surface is configured to maintain the foot member in continuous contact with the support surface from at least a heel-strike position to a mid-stance position during ambulation of the prosthetic foot to provide a substantially uniform progression of a center of pressure of the foot from heel-strike to mid-stance and a substantially smooth rollover.

17. The prosthetic foot of claim 15, wherein the foot member comprises a foot plate and a heel plate operatively coupled to the foot plate, the foot plate and the heel plate comprising discrete members.

18. The prosthetic foot of claim 17, wherein the heel plate comprises the concave contoured arch portion.

19. The prosthetic foot of claim 17, further comprising an adapter coupled to the foot plate, wherein the foot plate extends downward and forward from the adapter to a toe end, and wherein the heel plate contacts an underside of the foot plate and extends rearwardly therefrom to a heel end.

* * * * *